United States Patent [19]

Falkow et al.

[11] 4,358,535

[45] Nov. 9, 1982

[54] SPECIFIC DNA PROBES IN DIAGNOSTIC MICROBIOLOGY

[75] Inventors: Stanley Falkow, Seattle; Stephen L. Moseley, Kirkland, both of Wash.

[73] Assignee: Board of Regents of the University of Washington, Seattle, Wash.

[21] Appl. No.: 213,803

[22] Filed: Dec. 8, 1980

[51] Int. Cl.$^3$ ............................................. C12Q 1/70
[52] U.S. Cl. ..................................... 435/5; 23/230 B; 424/2; 424/8; 424/12; 424/13; 435/6; 435/34; 435/35; 435/36; 435/37; 435/38
[58] Field of Search ....................... 435/5, 6, 7, 29, 34, 435/35, 36, 37, 38, 39, 40; 23/230 B; 424/2, 8, 12, 13

[56] References Cited

U.S. PATENT DOCUMENTS

| | | | |
|---|---|---|---|
| 3,755,086 | 8/1973 | Heimer | 435/6 |
| 3,930,956 | 1/1976 | Juni | 435/6 |
| 4,038,143 | 7/1977 | Juni | 435/6 X |
| 4,275,149 | 6/1981 | Litman et al. | 435/6 X |

*Primary Examiner*—Robert J. Warden
*Attorney, Agent, or Firm*—Bertram I. Rowland

[57] ABSTRACT

Method and compositions for infectious disease diagnosis and epidemiology involving labeled nucleotide probes complementary to nucleic acid coding for a characteristic pathogen product. Clinical isolates are cultivated, expanding the number of microorganisms, the resulting colonies lysed, the genome normally denatured and then fixed. Alternatively, clinical samples (stool, sputum, pus, etc.) are spotted onto an inert support. The sample is treated in such a way that the DNA is liberated from microbes present in the sample and complexed onto the support. The DNA is normally denatured and fixed in this process. Subsequently, a labelled polynucleotide probe specific for a DNA sequence characteristic of a pathogenic product suspected of being present in the clinical sample is contacted with the fixed genomic single stranded nucleic acid under hybridizing conditions. Hybridization of probes to the single stranded nucleic acid is diagnostic of the presence of the pathogen.

20 Claims, No Drawings

SPECIFIC DNA PROBES IN DIAGNOSTIC MICROBIOLOGY

This invention was supported in part by the National Institutes of Health and the U.S. Army Research Development Command.

The invention described herein was made in the course of work under a grant or award from the United States Department of Health and Human Services.

BACKGROUND OF THE INVENTION

1. Field of the Invention

Current methods used in infectious disease diagnosis usually involve detection of bacterial products, particularly genetic products. These may be enzymes detected by biochemical methods or surface structures or other protein or in some instances carbohydrate substances detected immunologically. In many cases these tests are feasible only if sufficient numbers of living microorganisms are present. Other problems are also frequently encountered.

One of the problems encountered in present day diagnosis can be illustrated by diarrheal illness resulting from enterotoxigenic *E. coli*. One impediment to the diagnosis is the difficulty in differentiating toxin-producing *E. coli* from the harmless *E. coli* ordinarily found in the bowel of human or animals. Current methods to detect toxin-producing *E. coli* involve the detection of the toxin itself by biological and immunological assays. One form of toxin (heat labile toxin-LT) is detected by tissue culture or immunological assays. Another form of *E. coli* toxin (heat stable toxin-ST) is assayed in animals and involves sacrificing the animals and examining fluid accumulation in the gut. These techniques require manipulation of individual clinical isolates. Current screening for toxigenic *E. coli* is costly, inconvenient, and time consuming. This technique in one of its embodiments can get around that problem.

It would therefore be of great value to provide a simple and rapid screening capability which would allow for rapid simultaneous testing of large numbers of samples with a high degree of reliability. For commercial applications, it is desirable to have preprepared kits containing reagents which are standardized and optimized for sensitivity and accuracy.

2. Description of the Prior Art

Present methods for detecting the presence of enterotoxigenic *E. coli* may be found in Dean et al. J. Infect. Dis. 125:407–411, 1972; Guerrant et al., Infect. Immun. 10:310–327, 1974; Sack and Sack, ibid. 11:334–336, 1975; Volken et al. J. Clin. Microbiol. 6:439–444, 1977; Evans et al. Infect. Immun. 7:873–880, 1973; and Smith and Gyles, J. Med. Microbiol. 3:403–409, 1970. The genes and coding for the LT and ST have been isolated and described by Dallas et al., J. Bacteriol. 139:850–858, 1979, and So et al. Nature 277:453–456, 1979. The method of colony hybridization for isolation of cloned organisms having a specific gene is described by Grunstein and Hogness, Proc. Nat. Acad. Sci. USA. 72:3961–3965, 1975.

SUMMARY OF THE INVENTION

Pathogen-mediated disease is diagnosed employing labeled polynucleotide probes (DNA probes) specific for a gene encoding a product characteristic of the pathogen, either a cytoplasmic product or released product which may be characteristic toxins, for example. Particularly, a clinical sample or isolate suspected of containing the pathogen is transferred onto an inert porous support, for example, a nitrocellulose filter, and treated in such a way that the cells are localized. In certain circumstances, it may be appropriate to expand the cell numbers by placing the support on a nutrient medium, allowing colonies to form. The cells are then treated in such a way as to release their DNA and cause it to couple onto the support. Subsequent treatment causes a separation of the individual DNA strands of the genome. The strands are then contacted with labeled probes specific for the characteristic polynucleotide sequence under hybridization conditions. Hybridization of the probe to the single stranded polynucleotides from the pathogen is detected by means of the label. Various labels may be used which can provide for direct or indirect detection.

DESCRIPTION OF THE SPECIFIC EMBODIMENTS

A general diagnostic method is provided for detection of the pathogenic origin of disease. The method finds particular application in infectious disease diagnosis and epidemiology. The method is reasonably rapid, has a simple protocol, has reagents which can be standardized and provided as commercial kits, and allows for rapid screening of a large number of samples. In one embodiment of the invention, samples may be taken through part of the protocol in "the field" and conveniently returned to a distant laboratory for final completion of the diagnosis.

In carrying out the method, a clinical isolate suspected of containing the pathogen may be used directly or cultivated under conditions where clones are grown providing high multiplication of the pathogenic organism. After treating the genome to provide single stranded genomic nucleic acid and fixing the nucleic acid to a support, the affixed DNA or RNA is contacted with a labeled polynucleotide having a base sequence complementary to the coding or antisense strand of a gene coding for a product characteristic of the pathogen.

The primary reagent is the labeled probe. The probe may be RNA or DNA. The probe will normally have at least about 25 bases, more usually at least about 30 bases, and may have up to about 10,000 bases or more, usually having not more than about 5,000 bases. The probe sequence will be at least substantially complementary to a gene coding for a product characteristic of the pathogen, usually a cytoplasmic product or released product, particularly an excreted product. The probe need not have perfect complementarity to the sequence to which it hybridizes; there may by 30% or more of mismatched pairs. Cross hybridization which broadens the specificity of the reaction, may be a result of variable regions in the genes, mutations, a common probe for a plurality of microorganisms, alleles, or the like. Conditions that influence the formation of DNA hybrids are well known and described in detail in J. Bact. 115(3) 904–911, 1973 by Crosa, J. H., Brenner, D. J., and Falkow, Stanley.

Structural genes which may be characteristic of pathogens include genes coding for surface antigens, capsid proteins, toxins, exo- or endotoxins, enzymes, membrane proteins, and the like. Pathogenic products may include toxins, pyrogens, or the like. In some instances, genes other than structural genes may serve, e.g. regulatory genes.

Microorganisms which may be diagnosed include bacteria, viruses, fungi, protozoa, molds, etc. Among toxin producing microorganisms are bacteria, such as gram negative bacilli, e.g. Escherichia, Vibrio, Yersinia, Klebsiella and Salmonella. Species include *E. coli, Vibrio cholerae, Haemophilus ducrei,* Legionaire's bacillus. Other microorganisms of interest are those difficult to cultivate such as *Chlamydia trachomatis,* genital Herpes virus, Norwalk Agent, Rotavirus, Cytomegalovirus, *Campylobacter jejuni.*

The probe may be obtained from messenger RNA, from cDNA obtained by reverse transcription of messenger RNA with reverse transcriptase or by cleavage of the genome, conveniently by endonuclease digestion, followed by cloning of the gene or gene fragment in accordance with known techniques. See, for example, Kornberg, DNA Replication, W. H. Freeman and Co., San Francisco, 1980, pp 670–679; Dallas et al. supra; So et al., supra; So et al., Infect. Immun. 21:405–411, 1978. After isolation and characterization of the desired gene or DNA fragment, the gene or DNA fragment may be used for preparation of the probe or cloned for production of messenger RNA, which may then be used for preparation of the probe.

For the most part, the polynucleotide probe will be labeled with an atom or inorganic radical, most commonly using radionuclides, but also perhaps heavy metals. However, in some situations it may be feasible to employ an antibody which will bind specifically to the probe hybridized to the single stranded DNA of the pathogen. In this instance, the antibody would be labeled to allow for detection. The same types of labels which are used for the probe may also be bound to the antibody in accordance with known techniques.

Conveniently, a radioactive label may be employed. Radioactive labels include $^{32}P$, $^{3}H$, $^{14}C$, or the like. Any radioactive label may be employed which provides for an adequate signal and has sufficient half-life. Other labels include ligands, which can serve as a specific binding member to a labeled antibody, fluorescers, chemiluminescers, enzymes, antibodies which can serve as a specific binding pair member for a labeled ligand, and the like. A wide variety of labels have been employed in immunoassays which can readily be employed in the present assay. The choice of the label will be governed by the effect of the label on the rate of hybridization and binding of the probe to the genetic DNA. It will be necessary that the label provide sufficient sensitivity to detect the amount of DNA available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an $\alpha$-$^{32}P$-dNTP or terminal phosphate hydrolysis with alkaline phosphatase followed by labeling with radioactive $^{32}P$ employing $\gamma$-$^{32}P$-NTP and T4 polynucleotide kinase. Alternatively, nucleotides can be synthesized where one or more of the elements present are replaced with a radioactive isotope, e.g. hydrogen with tritium. If desired complementary labeled strands can be used as probes to enhance the concentration of hybridized label.

Where other radionuclide labels are involved, various linking groups can be employed. A terminal hydroxyl can be esterified, with inorganic acids, e.g. $^{32}P$ phosphate, or $^{14}C$ organic acids, or else esterified to provide linking groups to the label. Alternatively, intermediate bases may be substituted with activatable linking groups which can then be linked to a label.

Ligands and antiligands may be varied widely. Where a ligand has a natural receptor, namely ligands such as biotin, thyroxine, and cortisol, these ligands can be used in conjunction with labeled naturally occurring receptors. Alternatively, any compound can be used, either haptenic or antigenic, in combination with an antibody.

Enzymes of interest as labels will primarily be hydrolases, particularly esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g. luminol.

The probe is employed for hybridizing to a gene affixed to a water insoluble porous support. The single stranded nucleic acid is affixed. Depending upon the source of the nucleic acid, the manner in which the nucleic acid is affixed to the support may vary.

For unicellular organisms, a particularly useful technique is colony hybridization. See Grunstein and Hogness, supra. The clinical isolate or specimen is spotted or spread onto a filter to provide a plurality of individual portions. The filter is an inert porous solid support, e.g. nitrocellulose. The clinical isolate may be any excreta or physiological fluid, such as stool, urine, sputum, pus, serum, plasma, ocular lens fluid, spinal fluid, lymph, genital washings, or the like. The filter may be contacted with a nutrient source, to expand the numbers of the cells to form discrete colonies. The nutrients can diffuse to the cells, but the cells cannot diffuse away from their location on the filter. Conveniently, a microfilter is employed, which inhibits the passage of the cells through the filter and the filter placed on a nutrient gel, e.g. nutrient containing agar.

The cells are then treated to liberate their DNA (and/or RNA). If they were provided with nutrients to expand their numbers, after a sufficient time for the colonies to form, the filter is removed from the nutrient source and the cells lysed. Lysis conditions are devised such that the cells or colonies do not migrate and their DNA remains affixed in place on the surface where they were situated. The lysing and DNA denaturing as well as the subsequent washings can be achieved by placing the filter containing the cells or colonies, isolate side up, onto a bibulous support saturated with an appropriate solution for a sufficient time to lyse the cells and denature the DNA. For lysing, chemical lysing will conveniently be employed, usually dilute aqueous alkali e.g. 0.1 to 1 M NaOH. The alkali will also serve to denature the DNA. Other denaturation agents include, elevated temperatures, organic reagents, e.g. alcohols, amides, amines, ureas, phenols and sulfoxides or certain inorganic ions, e.g. thiocyanate and perchlorate.

After denaturation the filter is washed in an aqueous buffered solution, generally at a pH of about 6 to 8, usually 7. Of the many different buffers that may be used, tris is an example. One or more washings may be involved, conveniently using the same procedure as employed for the lysing and denaturation.

After the lysing, denaturing and washes have been accomplished, the DNA spotted filter is dried at an elevated temperature, generally from about 50° to 70° C. The DNA is now fixed in position and can be assayed with the probe when convenient. This fixing of the DNA for later processing has great value for the use of this technique in field studies, remote from laboratory facilities.

Hybridization may now be accomplished. The filter is incubated at a mildly elevated temperature for a sufficient time with the hybridization solution without the probe to thoroughly wet the filter. Various hybridization solutions may be employed, comprising from about 20 to 60 volume, preferably 30, percent of an inert polar organic solvent. A common hybridization solution employs about 50% formamide, about 0.5 to 1 M sodium chloride, about 0.05 to 0.1 M sodium citrate, about 0.05 to 0.2% sodium dodecylsulfate, and minor amounts of EDTA, ficoll (about 300–500 kdal), polyvinylpyrrolidone, (about 250–500 kdal) and serum albumin. (dal=-dalton) Also included in the hybridization solution will generally be from about 0.5 to 5 mg/ml of sonicated denatured DNA e.g. calf thymus or salmon sperm; and optionally from about 0.5 to 2% wt/vol glycine. Other additives may also be included, such as dextran sulfate of from about 100 to 1,000 kdal and in an amount of from about 8 to 15 weight percent of the hybridization solution.

The particular hybridization technique is not essential to the invention. Other hybridization techniques are described by Gall and Pardue (1969) Proc. Natl. Acad. Sci. 63:378–383 and John, Burnsteil and Jones (1969) Nature 223:582–587. As improvements are made in hybridization techniques they can readily be applied.

The amount of labeled probe which is present in the hybridization solution will vary widely, depending upon the nature of the label, the amount of the labeled probe which can reasonably bind to the filter, and the stringency of the hybridization. Generally, substantial excesses over stoichiometric of the probe will be employed to enhance the rate of binding of the probe to the fixed DNA.

Various degrees of stringency of hybridization will be employed. The more severe the conditions, the greater the complementarity that is required for hybridization between the probe and the ssDNA for duplex formation. Severity can be controlled by temperature, probe concentration, probe length, ionic strength, time, and the like. Conveniently, the stringency of hybridization is varied by changing the polarity of the reactant solution by manipulating the concentration of formamide in the range of 20% to 50%. Temperatures employed will normally be in the range of about 20° to 80° C., usually 30° to 75° C.

After the filter has been contacted with a hybridization solution at a moderate temperature for an extended period of time, the filter is then introduced into a second solution having analogous concentrations of sodium chloride, sodium citrate and sodium dodecylsulfate as provided in the hybridization solution. The time for which the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

With viruses, growing of the viruses and isolation and denaturation will usually be different from the treatment of the microbial pathogens. The viruses will usually be grown on an appropriate cellular lawn of cells susceptible to lysis by the target virus. After incubation on a nutrient containing gel and plaque formation resulting in individual viral colonies or clones, the isolation and fixing of the genome will vary depending on whether the genome is DNA or RNA, single or double stranded, linear or circular.

The viral capsid proteins may be removed using mild detergents, e.g. 1% sodium dodecylsulfate, proteases, e.g. pronase, or other conventional techniques. With linear dsDNA, capsid removal and denaturation can be achieved with mild alkali. With circular dsDNA, the DNA may be treated first with a nickase to provide at least one linear fragment, followed by denaturing conditions. With single stranded RNA, after removal of the capsid, no further treatment may be required. Capsid removal should avoid treatments, such as alkali treatment, which results in degradation of the RNA.

The following examples are offered by way of illustration and not by way of limitation.

EXPERIMENTAL

MATERIALS AND METHODS

Bacterial strains.

*E. coli* K-12 C600 (EWD299) contains a multicopy recombinant plasmid encoding LT, Dallas et al. J. Bacteriol. 139:850–858, 1979. Strain K-12 C600 (CLS-2) contains a multicopy recombinant plasmid encoding ST Lathe et al. Nature 284:473–474, 1980. Clinical isolates of *E. coli* producing ST, ST+LT, LT and nontoxigenic isolates were isolated from Peace Corps volunteers in Morocco and characterized. See Sack et al. Gastroenterology 76:1368–1373, 1979. Other strains of *E. coli* were isolated from patients with acute diarrhea at the International Centre for Diarrhoeal Disease Research, Bangladesh (ICDDR,B), Dacca, Bangladesh.

Standard assays for enterotoxin production.

LT was detected by the Chinese hamster overy (CHO) cell assay Guerrant et al., supra. ST production was detected by the infant mouse assay (Morris et al. J. Clin. Microbiol. 3:486–495, 1976). These assays are referred to as "standard assays" for enterotoxin production.

Plasmid DNA isolation.

Plasmid DNA was isolated as described by So et al. Infect. Immun. 21:405–411, 1978.

Preparation of $^{32}$P-labeled probe DNA.

"Probe DNA" intends radiolabeled, specific DNA fragments from enterotoxin genes which are used to probe for homologous DNA sequences in strains being assayed. LT probe DNA was prepared from EWD299 plasmid DNA, and consisted of a 0.5 megadal HindIII-generated fragment encoding a portion of the LT molecule. Dallas et al., supra. The ST probe DNA was prepared from CLS-2 plasmid DNA and consisted of a 157 base pair HinfI fragment encoding a portion of the ST molecule. Each DNA fragment was isolated by polyacrylamide gel electrophoresis of restricted DNA. The appropriate fragment was cut out of the gel, and the DNA removed from the polyacrylamide by electroelution. The isolated DNA fragments were phenol extracted twice, ethanol precipitated, and labeled in vitro with $\alpha$-$^{32}$P deoxynucleotide triphosphates by nick translation to a specific activity of 2.5–5×10$^7$ cpm/$\mu$g DNA.

Preparation and hybridization of nitrocellulose filters.

The method of Grunstein and Hogness, supra, was used with modification. Nitrocellulose discs (9 cm, BA-85, Schleicher and Schuell, Keene, N.H.) were boiled in water for two minutes, then individually wrapped in paper and autoclaved. A single sterile filter was placed on the surface of MacConkey agar and directly inoculated with isolated colonies or spotted with stool material. After overnight incubation at 37° C., the filter (on which colonies had formed) was removed from the agar. The filter was placed (colony side up) on a double layer of Whatman No. 3 paper saturated with 0.5 M NaOH. After ten minutes, the filter was transferred for a residence time of one minute to a double layer of Whatman No. 3 paper saturated with 1 M Tris, pH7. After two additional transfers on fresh 1 M Tris, pH7, saturated paper with residence times of one minute each, the filter was transferred to a double layer of Whatman No. 3 paper saturated with 1 M Tris, pH7, 1.5 M NaCl and allowed to stand for ten minutes. The filter was then removed from the Tris-NaCl, allowed to air dry, and baked overnight at 65° C.

Before performing in situ hybridization with radiolabeled DNA fragments, the filter was incubated at 37° C. for three hours in a plastic wrap (Saran Wrap) containing a sufficient volume of the following hybridization solution to thoroughly wet the filter: 50% formamide, $5 \times SSC$ ($1 \times SSC$ is 0.15 M NaCl, 0.015 M sodium citrate), 0.1% sodium dodecylsulfate (SDS), 1 mM EDTA, $1 \times$ Denhardt's solution (0.02% ficoll, 400 kdal; 0.02% polyvinylpyrrolidone, 360 kdal; 0.02% bovine serum albumin) (dal-dalton). The filter was then placed in fresh hybridization solution containing approximately $1 \times 10^5$ cpm/ml probe DNA (heat denatured) and 75 μg/ml heat denatured calf thymus DNA sheared to an average size of $2.5 \times 10^5$ dal by sonication. Hybridization was carried out for 24 hrs. at 37° C.

The filter was then washed in $5 \times SSC$, 0.1% SDS for 45 mins. at 65° C., rinsed in $2 \times SSC$ at room temperature, and allowed to air dry. The filter was exposed to Kodak Xomat-R X-ray film with a single DuPont Cronex Lightning-Plus intensification screen for 8-24 hrs. at $-70°$ C. The film was developed according to manufacturer's instructions.

EXAMPLE I

Two groups of patients were studied. For isolation of enterotoxigenic *E. coli* for comparison of the colony hybridization technique with standard assays, patients with acute diarrhea likely to be caused by enterotoxigenic *E. coli* were cultured. Stools or rectal swabs from these patients were streaked on MacConkey agar. For each patient, five lactose fermenting colonies typical of *E. coli* were picked for standard assay for enterotoxin production and for colony hybridization.

A second group of patients was selected for direct spotting of stool material on nitrocellulose for colony hybridization to establish that direct stool spotting on the filter is feasible. This group consisted of 50 consecutive patients admitted to the ICDDR,B intravenous rehydration ward over a period of two days. Stools or rectal swabs from each patient were directly spotted onto nitrocellulose filters overlayed by MacConkey agar (25 stools per filter). Each stool or rectal swab was also streaked onto MacConkey agar for isolation of colonies. Two isolated colonies and a pool of five colonies from each culture were assayed for enterotoxin production by standard methods.

Initially, a group of 30 clinical *E. coli* isolates previously characterized as producing ST, LT, ST+LT, or as nontoxigenic by standard techniques were examined by the colony hybridization technique. Stains were inoculated on two nitrocellulose filters for separate hybridization with the LT and ST probes. All seven LT producing strains (LT-only and ST+LT) were detected by the LT probe, while the ST probe detected five of seven ST strains and one of four ST+LT strains. None of 16 nontoxigenic stains reacted with either probe.

The colony hybridization method was then compared with the CHO cell and infant mouse assays for the ability to detect enterotoxigenic *E. coli* infections in persons with acute diarrhea. Patients at the ICDDR,B treatment center with symptoms suggestive of enterotoxigenic *E. coli* diarrhea were selected. Stools or rectal swabs were streaked onto MacConkey agar, and five *E. coli* colonies were selected from each stool for inoculation onto duplicate nitrocellulose filters, and for standard assay for LT and ST production. Enterotoxigenic *E. coli* from 12 patients were found by the standard assays. All 12 strains were detected by the colony hybridization technique as well, including one LT-only and ten ST+LT strains detected by the LT probe, and one ST-only strain detected by the ST probe. None of the ten ST+LT strains were detected by the ST probe.

The results are summarized as follows. Of 22 patients found to be infected with enterotoxigenic *E. coli*, strains from 18 were detected by hybridization. These included 12 of 13 patients infected with *E. coli* producing LT only or ST+LT and six of nine patients with ST-only strains. In addition, isolated colonies from the one patient infected with ST+LT *E. coli* that was not detected in the direct stool inoculation were individually inoculated on nitrocellulose and were detected by the LT probe. Twenty-eight patients were not infected with enterotoxigenic *E. coli* as determined by standard assays, and none of these was positive by colony hybridization.

The failure of the ST probe to detect all ST producing *E. coli* suggests that human isolates of *E. coli* can produce at least two heterologous heat stable toxins, which are detectable in the infant mouse assay. However, the genes coding for the heterologous heat stable toxins do not heteroduplex under the stringent conditions of the hybridization. Either a different probe, or milder hybridization conditions do provide for heteroduplexing without increasing false positives.

EXAMPLE II

The method has been used in its direct embodiment to examine patients suspected of suffering from nongonococcal urethiotis. Pus or vaginal secretion is spotted onto a nitrocellulose filter as described in the previous example.

Following an identical method of treatment of the filter, the filter was reacted with the common chlamydial plasmid from *C. trachomatis*, labelled with $^{32}P$. The isolation of this plasmid and its hybridization characteristics have been described by Lovett.

The subject invention provides a simple and practical technique requiring relatively inexpensive materials and reagents. The technique is suitable for screening a very large number of strains at a single time. The processed filters can be stored for at least 12 weeks before hybridization, allowing inoculation and processing of the filters in the field and subsequent storage and transport to a central laboratory for hybridization. Numerous samples may be spotted on the same filter and processed simultaneously, greatly increasing clinical efficiency. The technique therefore offers significant opportunities for large scale epidemiological and surveillance studies.

Preparation of large quantities of probe DNA is highly practicable today employing genetic engineering techniques. In many instances, the same probe will be capable of being used for rapid screening to detect a toxin gene from a number of sources. By appropriate choice of stringency and probes, one is able to initially determine the general character of the toxin, followed by a more definitive determination of the specific organism from which the toxin is derived. For detecting particular pathogens or pathogenic products, the toxin study described above is paradigmatic. Employing the same techniques, toxin and non-toxin-producing pathogens can be simply and rapidly determined.

Although the foregoing invention has been described in some detail by way of illustration and example for purposes of clarity of understanding, it will be obvious that certain changes and modifications may be practiced within the scope of the appended claims.

What is claimed is:

1. A method for detecting the presence of a pathogen in a clinical sample suspected of containing said pathogen, said method comprising:
   depositing said sample on an inert support;
   treating said sample to affix genetic material of any of said pathogen present in said sample to said support in substantially single stranded form at substantially the same site on said support where said sample was deposited;
   contacting said fixed single stranded genetic material with a labeled probe having a nucleotide sequence of at least about 25 bases at least substantially complementary to a nucleotide sequence of a structural gene characteristic of said pathogen, said contacting being under hybridizing conditions at a predetermined stringency; and
   detecting duplex formation on said support by means of said label.

2. A method according to claim 1, including the additional step of cultivating said deposited sample to produce at least one individual colony.

3. A method according to claims 1 or 2, wherein said depositing is performed by streaking or spotting.

4. A method according to claim 2, wherein said support is an inert porous filter and said cultivating comprises:
   maintaining said filter in contact with a nutrient gel; and said contacting comprises
   placing said filter on a bibulous material wetted with reagent solution capable of removing other than genetic material to leave single stranded genetic material.

5. A method according to claims 1, 2 or 4, wherein said pathogen is a unicellular organism.

6. A method according to claim 5, wherein said unicellular organism is a bacterium.

7. A method according to claims 1, 2 or 4, wherein said pathogen is a virus.

8. A method according to claims 1, 2 or 4, wherein said pathogen is a multicellular organism.

9. A method according to claims 1, 2 or 4, wherein said structural gene codes for an excreted product.

10. A method according to claims 1, 2 or 4, wherein said structural gene codes for a cytoplasmic product.

11. A method for detecting the presence of a unicellular pathogen in a sample suspected of containing said pathogen, said method comprising:
    depositing said sample on an inert porous filter as a plurality of individual portions;
    transferring said filter to a bibulous material wetted with a reagent solution capable of lysing said pathogen and denaturing the genetic material of said pathogen to provide single stranded DNA;
    heating said filter to fix said single stranded DNA at substantially the same site as the individual portion from which said genetic material is derived;
    contacting said fixed single stranded DNA with a labeled probe having a nucleotide sequence of at least about 25 bases at least substantially complementary to a nucleotide sequence of a structural gene characteristic of said pathogen under hybridizing conditions of a predetermined stringency,; and
    detecting duplex formation on said support by means of said label.

12. A method according to claim 11, including the step of:
    cultivating said individual portions on said inert porous filter by contacting said filter with a nutrient gel to produce individual colonies of said pathogen, and wherein said reagent solution is a dilute aqueous alkaline solution.

13. A method according to claims 11 or 12, wherein said label is a radionuclide.

14. A method according to claims 11 or 12, wherein said label is a fluorescent molecule.

15. A method according to claims 11 or 12, wherein said unicellular pathogen is a bacterium.

16. A method according to claim 15, wherein said label is a radionuclide.

17. A method for detecting the presence of a gram negative bacillus in a clinical isolate suspected of containing said bacillus, said method comprising:
    spotting said clinical isolate onto an inert porous filter;
    contacting said spotted inert porous filter with a nutrient gel, whereby nutrients diffuse to said bacillus in said spot, whereby a colony forms;
    transferring said filter supporting said colony onto a bibulous material containing a reagent solution for lysing said bacillus and denaturing the genome of said bacillus to provide single stranded DNA at substantially the same site as said colony;
    heating said filter to fix said single stranded DNA to said filter;
    contacting said filter with said fixed single stranded DNA, with a radioactively labeled probe having a nucleotide sequence of at least about 25 bases and at least substantially complementary to a nucleotide sequence of a structural gene characteristic of said bacillus under hybridizing conditions of a predetermined stringency; and
    detecting duplex formation on said support by means of said radioactive isotope.

18. A method according to claim 17, wherein said structural gene codes for a released product.

19. A method according to claim 18, wherein said released product is a toxin.

20. A method according to claims 17, 18 or 19, wherein said bacillus is enterotoxigenic *Escherichia coli*.

* * * * *

REEXAMINATION CERTIFICATE (504th)
United States Patent [19]
Falkow et al.

[11] B1 4,358,535
[45] Certificate Issued May 13, 1986

[54] SPECIFIC DNA PROBES IN DIAGNOSTIC MICROBIOLOGY

[75] Inventors: Stanley Falkow, Seattle; Stephen L. Moseley, Kirkland, both of Wash.

[73] Assignee: Board of Regents of the University of Washington, Seattle, Wash.

Reexamination Request:
No. 90/000,526, Mar. 12, 1984

Reexamination Certificate for:
Patent No.: 4,358,535
Issued: Nov. 9, 1982
Appl. No.: 213,803
Filed: Dec. 8, 1980

[51] Int. Cl.$^4$ .................... C12Q 1/70; C12Q 1/68
[52] U.S. Cl. ........................................ 435/5; 424/2; 435/6; 435/34; 435/35; 435/36; 435/37; 435/38; 436/501; 436/504; 935/78
[58] Field of Search ............................ 435/6

[56] References Cited

FOREIGN PATENT DOCUMENTS

2019408 10/1979 United Kingdom.
2034323 6/1980 United Kingdom.

OTHER PUBLICATIONS

"Persistent Viruses", ICN-UCLA Symposia on Molecular and Cellular Biology, vol. XI, pp. 181-188 by J. K. McDougall et al., 1978.
Galloway, D. A. et al., Nature, 302, 21-24 (3 Mar. 1983).
So, M. et al., Infection and Immunity, 21(2), 405-411 (Aug. 1978).
Wolf, H. et al., Nature New Biology, 244, 245-247 (1973).
"Oncogenesis and Herpesviruses", World Health Organization, International Agency for Research on Cancer, Proceedings of a Symposium held at Christ's College, Cambridge, England, 20-25 Jun. 1971, pp. 321-325 by H. Zur Hausen et al., 1972.
"Oncogenesis and Herpesviruses III", World Health Organization, International Agency for Research on Cancer, Proceedings of the Third International Symposium on Oncogenesis and Herpesviruses, Cambridge, Mass, USA, 25-29 Jul. 1977, pp. 739-744 by S. M. Lemon et al., 1978 and pp. 917-925 by K. W. Jones et al., 1978.
Grunstein, M. et al., Natl. Acad. Sci (USA) Proc. 72: 3961-3965 (1975).
Dallas, W.S. and Falkow, S. ("Dallas I") Molecular and Genetic Analysis of a DNA Sequence Encoding for Enterotoxin . . . , Thirteenth Joint Conference on Choler, The U.S.-Japan Cooperative Medical Science Program, Library of Medicine on Jan. 12, 1979).
Dallas, W.S.; Moseley, S.; Falkow, S. ("Dallas II") The Characterization of an Escherichia Coli Plasmid Determinant . . . , Plasmids of Medical Environmental and Commercial Importance, K.N. Timmis and A. Puhler, editors (Elsevier/North-Holland Biomedical Press, first shipment of book made on 11 October, 1979).
Reiser, J. Renart J. and Stark, G.R., "Transfer of Small DNA Fragments from Polyacrylamide Gels to Diazobengyloxymethyl Paper and Detection by Hybridization with DNA Probes", Biochemical and Biophysical Research Communications, vol. 85, No. 3, Dec. 14, 1978, pp. 1104-1112.
Huang, E-S. and Pagano, "Nucleic Acid Hybridization Technology and Detection of Proviral Genomes", Methods Viral, vol. 6, 1977, pp. 457-497.
Burrell, D.J.; Mackay, P.; Greenaway, P.J.; Hofschneider, P.H.; Murray, K. ("Burrell et al."). Nature, vol. 279, May 3, 1979, pp. 43-47.

Primary Examiner—Sidney Marantz

[57] ABSTRACT

Method and compositions for infectious disease diagnosis and epidemiology involving labeled nucleotide probes complementary to nucleic acid coding for a characteristic pathogen product. Clinical isolates are cultivated, expanding the number of microorganisms, the resulting colonies lysed, the genome normally denatured and then fixed. Alternatively, clinical samples (stool, sputum, pus, etc.) are spotted onto an inert support. The sample is treated in such a way that the DNA is liberated from microbes present in the sample and complexed onto the support. The DNA is normally denatured and fixed in this process. Subsequently, a labelled polynucleotide probe specific for a DNA sequence characteristic of a pathogenic product suspected of being present in the clinical sample is contacted with the fixed genomic single stranded nucleic acid under hybridizing conditions. Hybridization of probes to the single stranded nucleic acid is diagnostic of the presence of the pathogen.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 32–42:

In carrying out the method, a clinical [isolate] *sample* suspected of containing the pathogen may be used directly or cultivated under conditions where clones are grown providing high multiplication of the pathogenic organism. After treating the genome to provide single stranded genomic nucleic acid and fixing the nucleic acid to support, the affixed DNA or RNA is contacted with a labeled polynucleotide having a base sequence complementary to the coding or antisense strand of a gene coding for a product characteristic of the pathogen.

Column 4, lines 24–39:

For unicellular organisms, a particularly useful technique is colony hybridization. See Grunstein and Hogness, supra. The clinical isolate or specimen is spotted or spread onto a filter to provide a plurality of individual portions. The filter is an inert porous solid support, e.g. nitrocellulose. The clinical [isolate] *sample* may be any excreta or physiological fluid, such as stool, urine, sputum, pus, serum, plasma, ocular lens fluid, spinal fluid, lymph, genital washings, or the like. The filter may be contacted with a nutrient source, to expand the numbers of the cells to form discrete colonies. The nutrients can diffuse to the cells, but the cells cannot diffuse away from their location on the filter. Conveniently, a microfilter is employed, which inhibits the passage of the cells through the filter and the filter placed on a nutrient gel, e.g. nutrient containing agar.

AS A RESULT OF REEXAMINATION, IT HAS BEEN DETERMINED THAT:

Claim 4 is cancelled.

Claims 1, 2, 5, 7–12 and 17 are determined to be patentable as amended.

Claims 3, 6, 13–16 and 18–20, dependent on an amended claim are determined to be patentable.

1. A method for detecting the presence of a pathogen in a clinical sample *consisting essentially of excreta or physiological fluid* suspected of containing said pathogen, said method comprising:
   depositing said sample on an inert support;
   treating said sample *without cultivation* to affix genetic material of any of said pathogen present in said sample to said support in substantially single stranded form at substantially the same site on said support where said sample was deposited;
   contacting said fixed single stranded genetic material with a labeled probe having a nucleotide sequence of at least about 25 bases at least substantially complementary to a nucleotide sequence of a structural gene characteristic of said pathogen, said contacting being under hybridizing conditions at a predetermined stringency; and
   detecting duplex formation on said support by means of said label.

2. A method according to claim 1, [including the additional step of cultivating said deposited sample to produce at least one individual colony] *wherein said excreta or physiological fluid is stool, sputum or pus.*

5. A method according to claims 1[,] *or 2,* [or 4,] wherein said pathogen is a unicellular organism.

7. A method according to claims 1[,] *or 2,* [or 4,] wherein said pathogen is a virus.

8. A method according to claims 1[,] *or 2,* [or 4,] wherein said pathogen is a multicellular organism.

9. A method according to claims 1[,] *or 2,* [or 4,] wherein said structural gene codes for an excreted product.

10. A method according to claims 1[,] *or 2,* [or 4,] wherein said structural gene codes for a cytoplasmic product.

11. A method for detecting the presence of a unicellular pathogen in a *clinical* sample *consisting essentially of excreta or physiological fluid* suspected of containing said pathogen, said method comprising:
   depositing said sample on an inert porous filter as a plurality of individual portions;
   *without cultivation,* transferring said filter to a bibulous material wetted with a reagent solution capable of lysing said pathogen and denaturing the genetic material of said pathogen to provide single stranded DNA;
   heating said filter to fix said single stranded DNA at substantially the same site as the individual portion from which said genetic material is derived;
   contacting said fixed single stranded DNA with a labeled probe having a nucleotide sequence of at least about 25 bases at least substantially complementary to a nucleotide sequence of a structural gene characteristic of said pathogen under hybridizing conditions of a predetermined stringency [,]; and
   detecting duplex formation on said support by means of said label.

12. A method according to claim 11, *wherein said excreta or physiological fluid is stool, sputum or pus* [including the step of:
   cultivating said individual portions on said inert porous filter by contacting said filter with a nutrient gel to produce individual colonies of said pathogen, and wherein said reagent solution is a dilute aqueous alkaline solution].

17. A method for detecting the presence of a gram negative bacillus in a clinical [isolate] *sample comprising excreta or physiological fluid* suspected of containing said bacillus, said method [comprising] *consisting essentially of:*
   spotting said clinical [isolate] *sample* onto an inert porous filter;
   [contacting said spotted inert porous filter with a nutrient gel, whereby nutrients diffuse to said bacillus in said spot, whereby a colony forms;]

*without cultivation,* transferring said filter [supporting said colony] onto a bibulous material containing a reagent solution for lysing said bacillus and denaturing the genome of said bacillus to provide single stranded DNA at substantially the same site as said [colony] *sample;* heating said filter to fix said single stranded DNA to said filter;

contacting said filter with said fixed single stranded DNA, with a [radioactively] *probe* labeled [probe] *with a radioactive isotope* having a nucleotide sequence of at least about 25 bases and at least substantially complementary to a nucleotide sequence of a structural gene characteristic of said bacillus under hybridizing conditions of a predetermined stringency; and detecting duplex formation on said support by means of said radioactive isotope.

\* \* \* \* \*